United States Patent [19]

Fukuda et al.

[11] 4,353,255
[45] Oct. 12, 1982

[54] METHOD FOR DETERMINING SHAPE OF CRACK

[75] Inventors: Yoshio Fukuda, Hitachi; Kunio Enomoto; Tsutomu Masumoto, both of Tokaimura, all of Japan

[73] Assignee: Hitachi, Ltd., Tokyo, Japan

[21] Appl. No.: 222,141

[22] Filed: Jan. 2, 1981

[30] Foreign Application Priority Data

Jan. 7, 1980 [JP] Japan .................................... 55/127

[51] Int. Cl.³ ......................................... G01N 29/04
[52] U.S. Cl. ..................................... 73/587; 364/507
[58] Field of Search .......................... 73/587; 364/507

[56]  References Cited
U.S. PATENT DOCUMENTS 3,985,024  10/1976  Horak ................................. 73/587
4,033,179  7/1977  Romrell ......................... 364/507 X Primary Examiner—James J. Gill
Attorney, Agent, or Firm—Antonelli, Terry & Wands

[57] ABSTRACT

AE signals due to a crack developed in a metal test object are detected by a number of AE sensors mounted on the metal test object. Based on time differences between the signals from the respective AE sensors, crack source points are determined. Then, based on the crack source points, a crack source plane is determined. The crack source plane is divided into a number of areas and a point of maximum number of crack source points in each of the areas is determined. Based on the points of maximum number of crack source points in the respective areas, a shape of the crack in the test object is determined.

6 Claims, 10 Drawing Figures

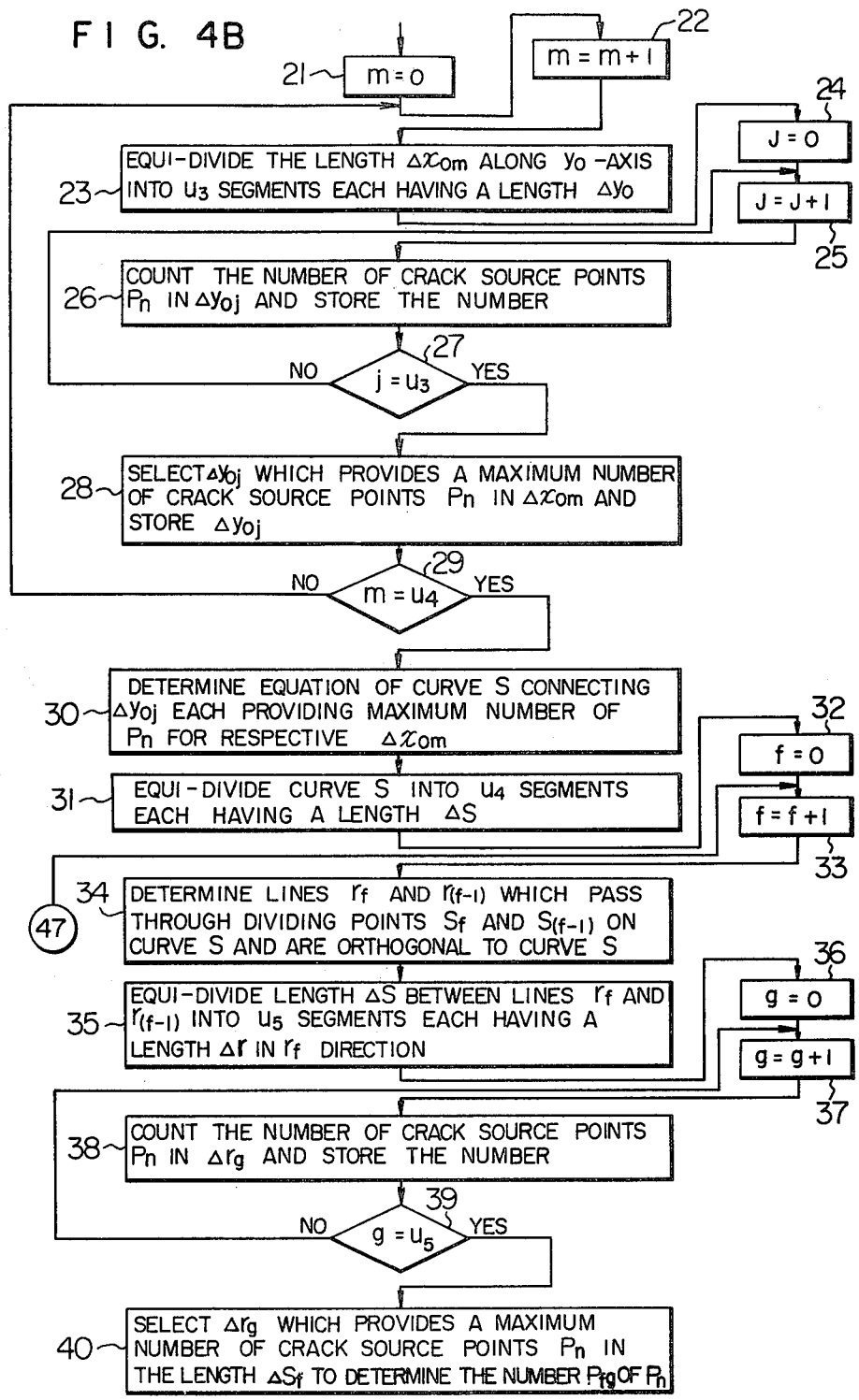

DISTANCE IN LINE $r_f$ DIRECTION

METHOD FOR DETERMINING SHAPE OF CRACK

The present invention relates to a method for determining a shape of crack, and more particularly to a method for determining a shape of crack using AE (acoustic emission) sensors which detect acoustic emissions produced when a metal is subjected to plastic deformation, shearing or friction.

An AE device which detects the occurrence of a crack developed in a metal by an AE sensor has been proposed. In a known AE device (disclosed in Japanese Published Examined Patent Application 53-21673), a number of AE sensors are mounted on a surface of a test object such as a vessel, crack is located based on signals from the AE sensors, and positions of source of acoustic emissions are indicated on an orthogonal coordinate. In case of fatigue crack, acoustic emissions developed by the friction of cracks previously developed under repetitive load, acoustic emissions developed by the shear of sheared ends and acoustic emissions developed by the plastic deformation ahead of the crack ends are mixed so that the AE signals distribute around the crack ends. It is, therefore, impossible to determine the shape of the crack.

It is an object of the present invention to determine the shape of the crack with a high accuracy.

The present invention is characterized by determining a crack source plane based on points of source of the acoustic emissions in the test object and determining the shape of the crack in the crack source plane based on a distribution of the points of source of the acoustic emissions.

The present invention will now be explained in conjunction with the accompanying drawings, in which:

FIGS. 4A, 4B and 4C show flow charts for operations carried out in a computer shown in FIG. 1;

Figure 1:
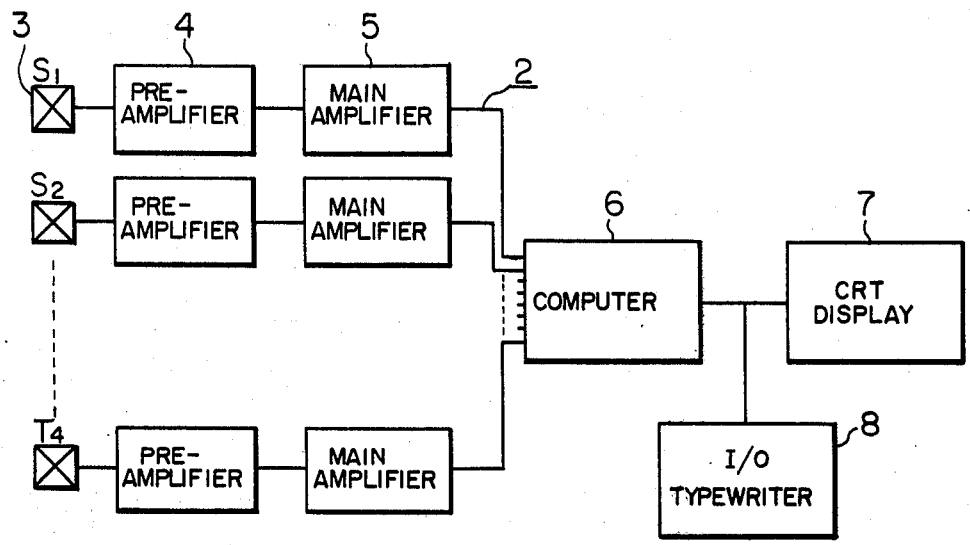
FIG. 1 shows a system diagram of a crack end position detecting device to which a preferred embodiment of the present invention is applied.
Figure 2:
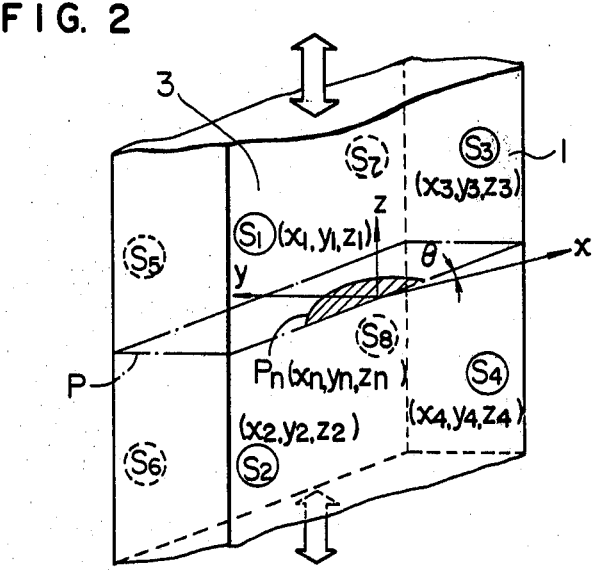
FIG. 2 illustrates a mounting condition of AE sensors shown in FIG. 1 on a test object.

Referring to FIG. 1 and FIG. 2, a preferred embodiment of the present invention is now explained. A crack shape detecting device 2 comprises a number of AE sensors 3, a computer 6 and a CRT display 7. Each of the AE sensors 3 is coupled to the computer 6 through a pre-amplifier 4 and a main amplifier 5. Numeral 8 denotes an I/O typewriter. The k number of AE sensors 3 are mounted at preselected positions on a surface of a test object such as a metal plate 1, as shown in FIG. 2. Symbols $S_1$–$S_8$ represent the AE sensors 3. As shown in FIG. 2, coordinates of mounting positions of the AE sensors $S_1$–$S_4$ in an orthogonal coordinate having x-axis, y-axis and z-axis are represented by $(x_1, y_1, z_1)$, $(x_2, y_2, z_2)$, $(x_3, y_3, z_3)$ and $(x_4, y_4, z_4)$, respectively.

Figure 3:
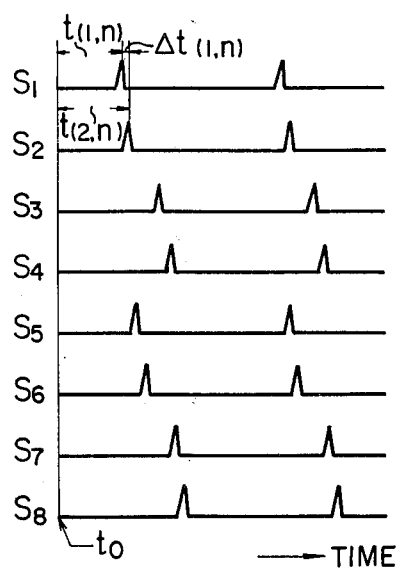
FIG. 3 shows waveforms of output signals produced from the AE sensors shown in FIG. 2.

The detection of the crack shape by the crack shape detecting device 2 is now explained in detail. Let us assume that a crack occurs at a point $P_n (x_n, y_n, z_n)$ and acoustic emissions are generated therefrom. The acoustic emissions developed are detected by the AE sensors $S_1$–$S_8$ which produce pulsive AE signals as shown in FIG. 3. Because of the difference of distances between the crack source point $P_n$ and the positions of the AE sensors $S_1$–$S_8$, elapsed times $t_{(k, n)}$ measured from a reference time point $t_o$ to time points at which the AE signals are produced by the k (eight in FIG. 2) AE sensors are different as shown in FIG. 3. The AE signals produced by the AE sensors $S_1$–$S_8$ are applied to the computer 6 via the preamplifiers 4 and the main amplifiers 5. An output from the computer 6 is displayed on the CRT display 7.

Figure 4A:
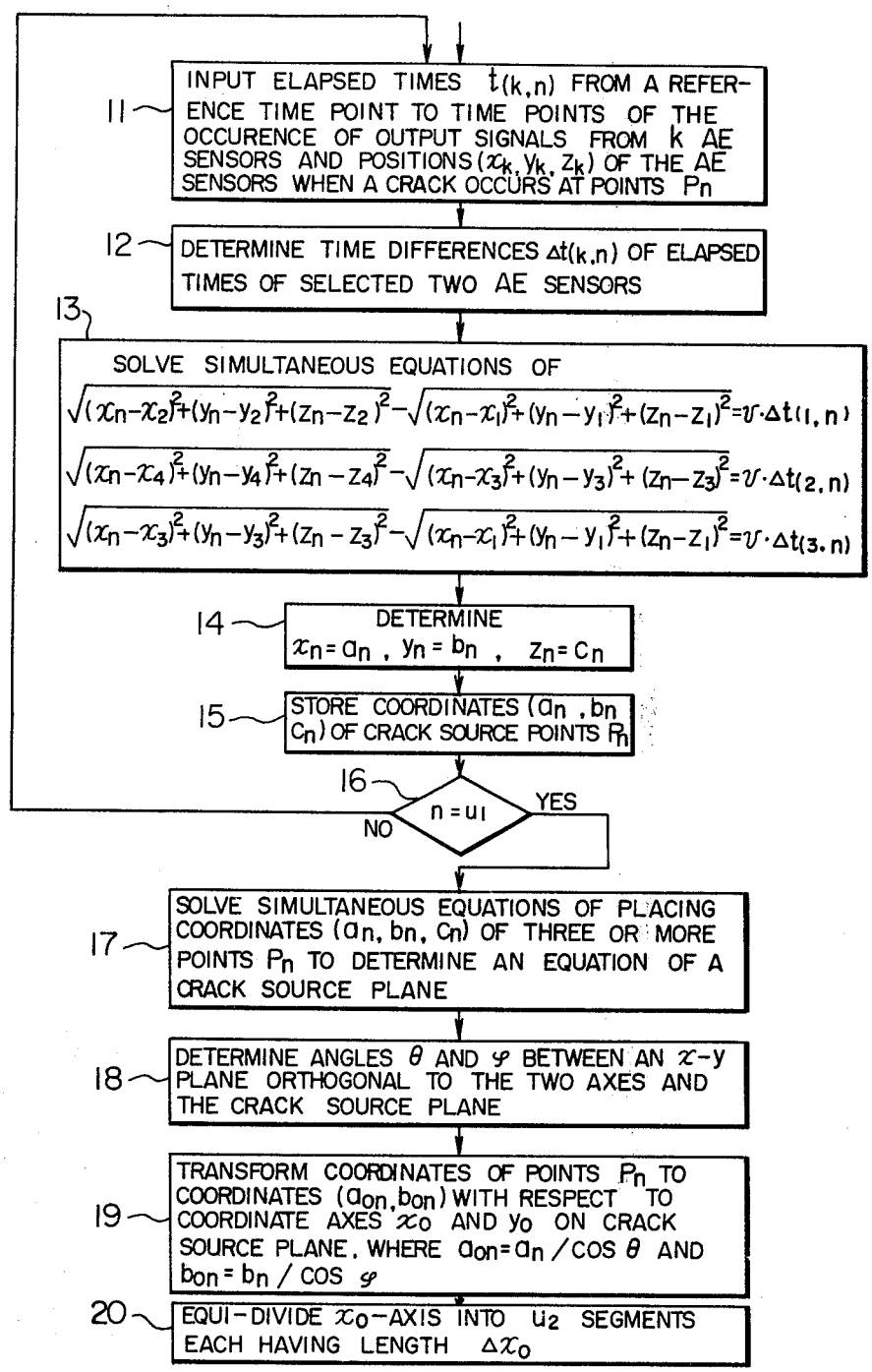
Figure 4C:
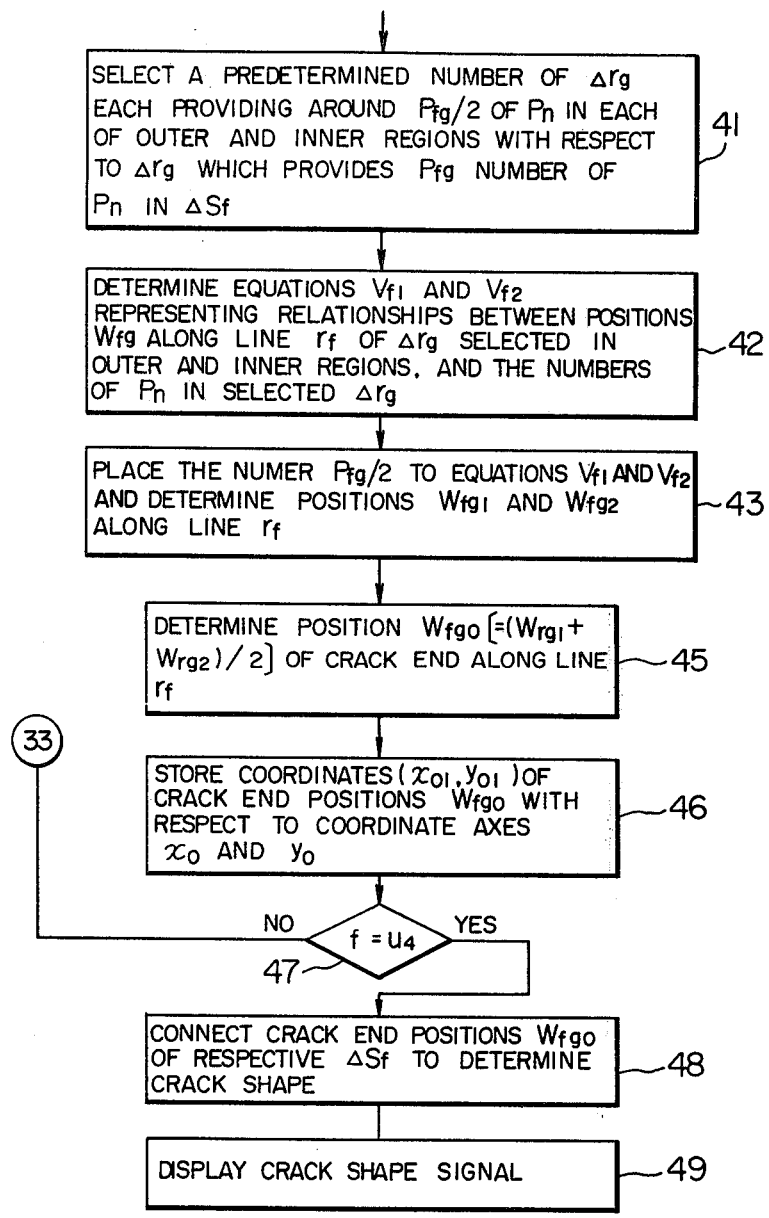

Referring to FIGS. 4A, 4B and 4C, the operation of the computer 6 is explained. The elapsed times $t_{(k, n)}$ from the reference time point $t_o$ to the time points at which the k AE sensors produce the output when the crack occurs at the point $P_n$ and the coordinates $(x_k, y_k, z_k)$ of the mounting positions of the AE sensors are inputted to the computer 6 (step 11). A time difference $\Delta t_{(k, n)}$ between the elapsed times of any two of the AE sensors is determined (step 12). For example, a time difference $\Delta t_{(1, n)}$ between the elapsed times of the AE sensors $S_1$ and $S_2$ is determined from $[t_{(1, n)} - t_{(2, n)}]$. At a step 13, based on the time difference $\Delta t_{(k, n)}$ of the elapsed times, the crack source point $P_n$ is determined. More particularly, a difference between distances from any two of the AE sensors and the crack source point $P_n$ is given by $v \cdot \Delta t_{(k,n)}$, where v is a sound velocity in the test object. Accordingly, a coordinate $(x_n, y_n, z_n)$ of the crack source point is determined by resolving the following simultaneous equations:

$$\sqrt{(x_n - x_2)^2 + (y_n - y_2)^2 + (z_n - z_2)^2} - \\ \sqrt{(x_n - x_1)^2 + (y_n - y_1)^2 + (z_n - z_1)^2} = v \cdot \Delta t_{(1,n)}$$

$$\sqrt{(x_n - x_4)^2 + (y_n - y_4)^2 + (z_n - z_4)^2} - \\ \sqrt{(x_n - x_3)^2 + (y_n - y_3)^2 + (z_n - z_3)^2} = v \cdot \Delta t_{(2,n)}$$

$$\sqrt{(x_n - x_3)^2 + (y_n - y_3)^2 + (z_n - z_3)^2} - \\ \sqrt{(x_n - x_1)^2 + (y_n - y_1)^2 + (z_n - z_1)^2} = v \cdot \Delta t_{(3,n)}$$

(3)

where $\Delta t_{(1,n)}$ is a difference between the elapsed times for the AE sensors $S_1$ and $S_2$, $\Delta t_{(2,n)}$ is a difference between the elapsed times for the AE sensors $S_3$ and $S_4$, and $\Delta t_{(3,n)}$ is a difference between the elapsed times for the AE sensors $S_1$ and $S_3$. The preceding term and the succeeding term in the left side of the equation depend on the magnitude of the elapsed time $t_{(k,n)}$. If the elapsed time $t_{(k,n)}$ for the AE sensor (k) is shorter than the elapsed time $t_{(k-1,n)}$ for the AE sensor (k−1), the distance from the AE sensor (k) to the crack source point $P_n$ is to be subtracted from the distance from the AE sensor (k−1) to the crack source point $P_n$. By resolving the above simultaneous equations, $x_n = a_n$, $y_n = b_n$ and $z_n=c_n$ are determined step (4). The $x_n=a_n$, $y_n=b_n$ and $z_n=c_n$ represent x, y and z axes positions of the crack source points $P_n$. The coordinates ($a_n$, $b_n$, $c_n$) of the crack source points $P_n$ are then stored (step 15). At a step 16, it is determined if the number n of the crack source points $P_n$ has reached a predetermined number $u_1$. If the number n is smaller than the number $u_1$, the steps 11-15 are repeated. If the number of the crack source points is small, a larger error will be included in determining crack end positions from the distribution of the crack source points.

When the number n reaches $u_1$, an operation of a step 17 is carried out. A coordinate ($a_n$, $b_n$, $c_n$) of a mean position derived by averaging the crack source points $P_n$ in three or more predetermined areas is substituted to the following equation (2);

$$\alpha x + \beta y + \gamma z + \delta = 0 \qquad (2)$$

to form simultaneous equations, which are then solved to determine an equation of a crack source plane P. Then, angles $\theta$ and $\rho$ between the (x, y) plane orthogonal to the z-axis and the crack source plane P are determined (step 18), where $\theta$ is the angle to the x-axis and $\rho$ is the angle to the y-axis. The coordinates ($a_n$, $b_n$, $c_n$) of the crack source points $P_n$ are transformed to coordinates ($a_{on}$, $b_{on}$) of coordinate axes $x_o$ and $y_o$ on the crack source plane P (step 19). The transform is carried out in accordance with the following equations (3) and (4). A direction normal to the crack source plane P is a coordinate axis $z_o$. Since the crack source points exist on the crack source plane P, $z_o$ is zero.

$$a_{on}=a_n/\cos\theta \qquad (3)$$

$$b_{on}=b_n/\cos\rho \qquad (4)$$

Figure 5:
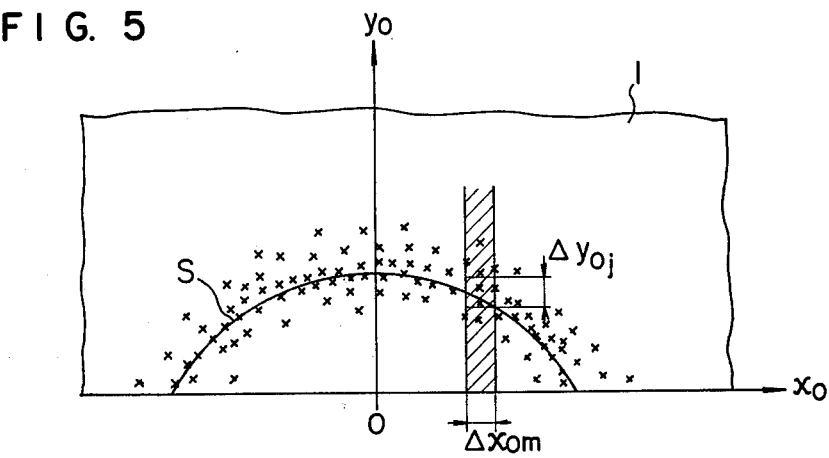
FIG. 5 illustrates an approximated crack ends.
Figure 6:
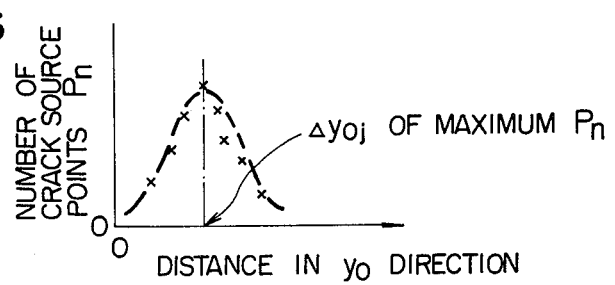
FIG. 6 shows a characteristic curve representing a relationship between a distance along a $y_o$ axis and the number of crack source points $P_n$ within a width of $\Delta x_{om}$.

As shown in FIG. 5, the $x_o$-axis is equi-divided, starting from a point of $x_o=0$, into $u_2$ segments each having a length $\Delta x_o$ (step 20). At a step 21, m is set to zero, and at a step 22, m is set to (m+1). At a step 23, the length $\Delta x_{om}$ is equi-divided along the $y_o$-axis starting from a point of $y_o=0$ into $u_3$ segments each having a length $\Delta y_o$. At a step 24, J is set to zero, and at a step 25, J is set to (J+1). The number of the crack source points $P_n$ in $\Delta y_{oj}$ is counted and stored (step 26). At a step 27, it is determined if j=$u_3$. If j<$u_3$, the steps 25 and 26 are repeated for the area $\Delta y_{oj}$ and the number of the crack source points $P_n$ in the area $y_{oj}$ is counted and stored. When j reaches $u_3$, the process moves to a step 28. As shown in FIG. 6, $\Delta y_{oj}$ which provides a maximum number of the crack source points $P_n$ in $\Delta x_{om}$ is selected and the position of $\Delta y_{oj}$ is stored (step 28). At a step 29, it is determined if m=$u_2$. If m<$u_2$, the steps 22, 23, 24, 25, 26, 27 and 28 are repeated. The positions of $\Delta y_{oj}$ each of which provides a maximum number of the crack source points $P_n$ in each $\Delta x_{om}$ are approximated crack end positions. If m reaches $u_2$ at a step 29, the process moves to a step 30. A curve S (FIG. 5) which envelopes the approximated crack end positions of the respective $\Delta x_{om}$ is determined by a minimum square method. The curve S represents an approximated crack shape.

Figure 7:
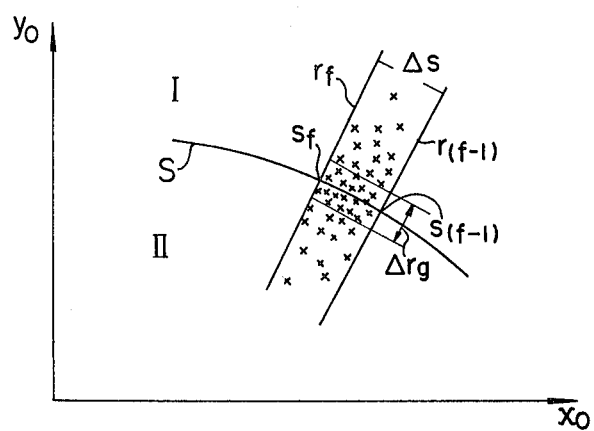
FIG. 7 illustrates a process for determining a distribution of the crack source points, within a width of $\Delta S$ normal to a curve S which envelopes the approximated crack ends.

At those portions where an angle between a line tangential to the curve S and the $y_o$-axis is small, the positions of the approximated crack ends determined by the above process include large errors. Accordingly, more exact crack end positions are determined in the following manner. The curve S is equi-divided into $u_4$ segments each having a length $\Delta S$ (step 31). At a step 32, f is set to zero, and at a step 33, f is set to (f+1). Lines $r_f$ and $r_{(f-1)}$ which pass through dividing points $S_f$ and $S_{(f-1)}$, respectively, on the curve S and are orthogonal to the curve S are determined (step 34). A distance $\Delta S_f$ between the lines $S_f$ and $S_{(f-1)}$ is equi-divided along the line $r_f$ into $u_5$ segments each having a length $\Delta r$ (step 35). At a step 36, g is set to zero, and at a step 37, g is set to (g+1). The number of the crack source points $P_n$ in the length $\Delta r_g$ is counted and stored (step 38). At a step 39, it is determined if g=$u_5$. If g<$u_5$, the steps 37 and 38 are repeated. If g=$u_5$, the process moves to a step 40. The $\Delta r_g$ which provides a maximum number of the crack source points $P_n$ in the length $\Delta S_f$ is selected and the maximum number $P_{fg}$ of the crack source points $P_n$ is stored (step 40). In an outer region I and an inner region II (FIG. 7) with respect to the $\Delta r_g$ which provides the maximum number $P_{fg}$ in the length $\Delta S_f$, a predetermined number (e.g. 15) of $\Delta r_g$ each having around $P_{fg}/2$ crack source points $P_n$ are selected (step 41). Equations $V_{f1}$ and $V_{f2}$ (FIG. 8) which represent the relationships between positions $W_{fg}$, along the line $r_f$, of the $\Delta r_g$ selected from the outer region and the inner region, and the numbers of $P_n$ in the selected $\Delta r_g$ are determined (step 42). The number $P_{fg}/2$ is placed in the equations $V_{f1}$ and $V_{f2}$ to determine the linear positions $W_{fg1}$ and $W_{fg2}$ corresponding to the number $P_{fg}/2$ (step 43). The crack end position $W_{fgo}$ in the direction of the line $r_f$ is determined from the following equation (5) (step 45).

$$W_{fgo}=(W_{fg1}+W_{fg2})/2 \qquad (5)$$

Figure 8:
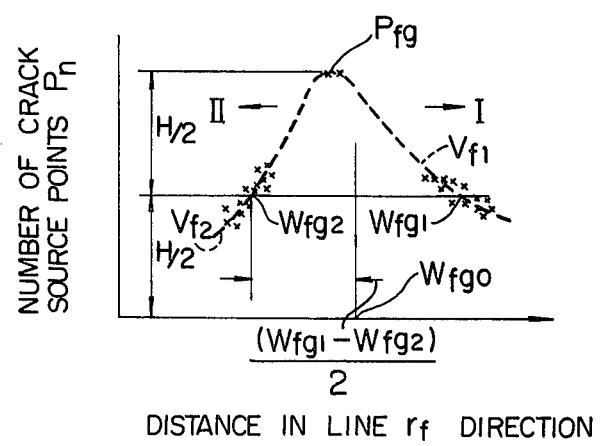
FIG. 8 illustrates a process for determining by a statistic analysis the crack ends based on the distribution of the crack source points.

The operation in the steps 41 to 45 determines a statistical representative value (one half of half value width) based on statistical analysis. The position $W_{fgo}$ of the crack end in the direction of the line $r_f$ is shown in FIG. 8. In accordance with the above process, the position $W_{fgo}$ of the crack end in the direction of the line $r_f$ can be determined with a high accuracy. A coordinate ($x_{of}$, $y_{of}$) of the crack end position $W_{fgo}$ with respect to the coordinates $x_o$ and $y_o$ is stored (step 46). At a step 47, it is determined if f=$u_4$. If f<$u_4$, the steps 33-47 are repeated. When f reaches $u_4$, the process moves to a step 48. At the step 48, the crack end positions $W_{fgo}$ for the respective $\Delta S_f$ are connected to define the crack shape. A signal representing the crack shape is applied to the display 7 (step 49). The display 7, when it receives the crack shape signal, displays the crack shape on a screen by an X-Y plotter. In this manner, the crack shape can be non-destructively determined with a high accuracy.

By displaying on the display 7 the crack end positions stored in the step 46, the crack end positions can be determined. It is also possible to indicate the positions on a sheet by a printer instead of the display 7.

By periodically sampling the output signals from the AE sensors, determining the crack shape by the process described above and comparing it with a previously determined crack shape, it is possible to determine a process of crack.

In the embodiment explained above, the approximated crack shape is determined based on the positions of $\Delta y_{oj}$ which provide the maximum numbers of the crack source points $P_m$ in $\Delta x_{om}$; alternatively, the approximated crack shape may be determined based on the statistical representative values described above. In this case, instead of the step 28 in the embodiment described above, the steps 40-46 are carried out. In the steps 40-46, S is substituted by $x_o$, r is substituted by $y_o$, f is substituted by m and g is substituted by j. A formula of a curve S derived by connecting $W_{mjo}$ of the respective $\Delta x_{om}$ is defined. This method of determining the approximated crack shape improves the accuracy of determining the crack shape.

When the crack exists within the metal plate 1 without opening to the surface of the metal plate 1 as shown in FIG. 2, a peak number, instead of the maximum number of the crack source points $P_n$ is used. That is, the maximum number in the steps 28, 30 and 40 is substituted by the peak number. In this manner a crack shape of closed loop such as ellipsoidal shape which exists within the metal plate 1 can be determined with a high accuracy. Since the maximum number is the largest one among the peak numbers, only one exists in the length $\Delta x_{om}$. In the closed loop crack, there are two $y_{oj}$ positions which provide peak numbers of the crack source points $P_n$ in the length $\Delta x_{om}$. Accordingly, when only the $\Delta y_{oj}$ position which provides the maximum number of the crack source points $P_n$ in the length $\Delta x_{om}$, the crack shape cannot be accurately determined.

In the embodiment described above, by omitting the steps 31–48 and displaying the shape of the curve S determined at the step 30 on the display 7, the crack shape of the test object can be determined. Again, in this case, the detection accuracy of the crack shape is improved if the curve S is determined using the statistical representative values.

The present invention is applicable to the test object of tubular shape or other complex shape. The present invention is also applicable to the detection of the crack shape developed in a vessel or pipe mounted in an assembled plant.

In accordance with the present invention, the shape of the crack which exists inside the test object can be non-destructively detected with a high accuracy.

What is claimed is:

1. A method for detecting a shape of a crack comprising the steps of detecting acoustic emissions produced due to the crack developed in a test object by a plurality of acoustic emission detecting means mounted on said test object, determining positions of crack source points in said test object based on differences in time points of signals produced by said acoustic emission detecting means, determining a crack source plane based on the positions of said crack source points, and determining the shape of the crack in said crack source plane based on a distribution of said crack source points.

2. A method according to claim 1, further comprising the steps of defining an x-axis and a y-axis orthogonal to each other in said crack source plane, determining first positions each providing a peak number of crack source points along the y-axis in each of n first divided areas which are derived by dividing said crack source plane into n areas along the x-axis, and determining the shape of the crack in said crack source plane based on said first positions.

3. A method according to claim 2, further comprising a step of displaying a curve connecting said first positions of said first divided areas of said crack source plane.

4. A method according to claim 1, further comprising the steps of defining an x-axis and a y-axis orthogonal to each other in said crack source plane, determining two second positions each providing one half of a peak number of the crack source points along the y-axis in each of n first divided areas derived by dividing said crack source plane into n areas along the x-axis, determining third positions in said first divided areas each of which is at equi-distance from said two second positions, and determining the shape of the crack in said crack source plane based on said third positions in said first divided areas.

5. A method according to claim 4, further comprising a step of displaying a curve connecting said third positions in said first divided areas of said crack source plane.

6. A method according to claim 2 or 4, further comprising the steps of dividing a curve connecting said first positions or said second positions in said first divided areas into m segments, determining two fourth positions each providing one half of a peak number of the crack source points in a direction orthogonal to said segment in each of second divided areas defined by two lines orthogonal to said segment and passing through the opposite ends of said segment in said crack source plane, determining fifth positions each of which are equi-distance from said two fourth positions in each of said second divided areas, and determining the shape of the crack in said crack source plane based on said fifth positions in said second divided areas.

* * * * *